United States Patent [19]

Milne

[11] Patent Number: 5,704,788
[45] Date of Patent: Jan. 6, 1998

[54] DENTAL IMPLANT ABUTMENT SCREW LOCK

[76] Inventor: Robert H. Milne, 700 NE. Multnomah, Portland, Oreg. 97232

[21] Appl. No.: 799,432

[22] Filed: Feb. 12, 1997

[51] Int. Cl.$^6$ ............................................. A61C 8/00
[52] U.S. Cl. ............................................. 433/173; 433/172
[58] Field of Search .................................. 433/172, 173, 433/174, 175, 176

[56] References Cited

U.S. PATENT DOCUMENTS

| | | | |
|---|---|---|---|
| 5,015,186 | 5/1991 | Detsch | 433/173 |
| 5,049,073 | 9/1991 | Lauks | 433/173 |
| 5,100,323 | 3/1992 | Friedman et al. | 433/173 |
| 5,106,300 | 4/1992 | Voitik | 433/173 |
| 5,108,288 | 4/1992 | Perry | 433/173 |
| 5,125,840 | 6/1992 | Durr et al. | 433/173 |
| 5,169,308 | 12/1992 | Kvist | 433/173 |
| 5,302,127 | 4/1994 | Crisio | 433/173 |
| 5,312,253 | 5/1994 | Chalifoux | 433/173 |
| 5,336,090 | 8/1994 | Wilson, Jr. et al. | 433/173 |
| 5,350,300 | 9/1994 | Gallais | 433/173 |
| 5,527,182 | 6/1996 | Willoughby | 433/173 |

*Primary Examiner*—John J. Wilson
*Attorney, Agent, or Firm*—Olson & Olson

[57] ABSTRACT

A dental implant is formed of an implant fixture for installation in the jawbone, an abutment secured non-rotationally to the implant fixture by interengaging connector components, and a coping screw removably securing the implant fixture and abutment together. To prevent unintended loosening of the coping screw, the non-circular shank of a locking member is inserted in a correspondingly shaped bore in the coping screw and laterally extending locking keys on the head of the locking member are captured in longitudinal grooves in the abutment, whereby the coping screw is secured positively against loosening.

8 Claims, 1 Drawing Sheet

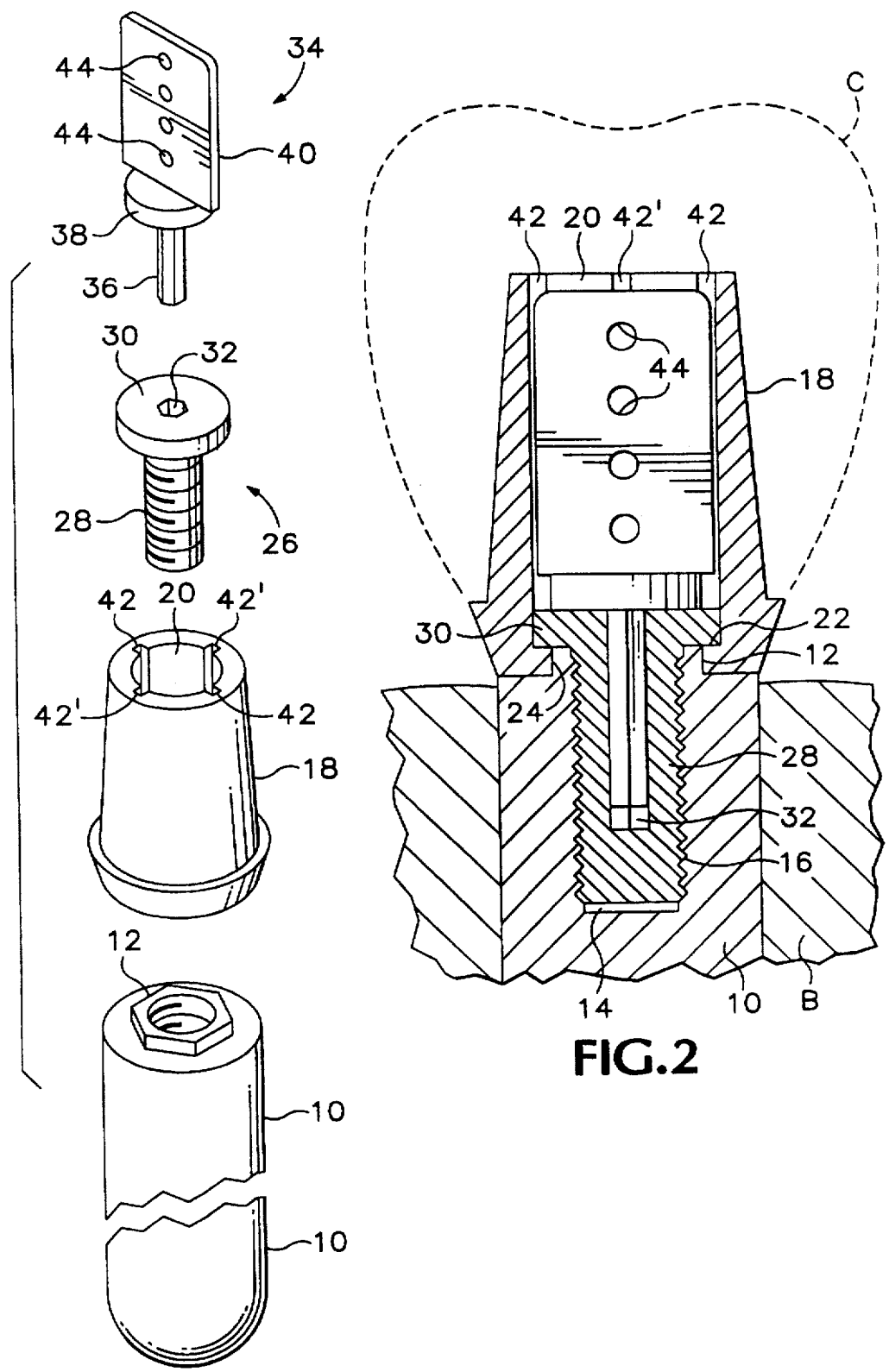

DENTAL IMPLANT ABUTMENT SCREW LOCK

BACKGROUND OF THE INVENTION

This invention relates to dental implants, and more particularly to a locking mechanism for securing the coping screw of an implant abutment positively against loosening.

Dental implants currently are comprised of an implant fixture that is inserted into the jaw bone, an abutment that mounts a dental prosthesis, and a coping screw that secures the abutment to the implant fixture. The implant fixture may be a metal screw, but preferably is a metal cylinder. The abutment is of metal and a dental prosthesis is secured to the abutment by cement or screws. The dental prosthesis may be a crown, a bridge, or a device for securing removable dentures.

It is a well recognized problem with dental implants using a coping screw to secure the abutment to the implant, that the screw can become loosened. Loosening of this screw can cause a myriad of problems including loss of the restoration or stripping of the screw threads. Sometimes the fatigue of the metal will increase sufficiently if the coping screw loosens so that abutments can fracture or the coping screw can fracture. If the coping screw loosens and the abutment and the prosthesis is cemented onto the abutment, one has a very difficult time in separating the abutment and the prosthesis from the juncture. This can result in significant damage to the implant fixture and can require cutting off the prosthesis and refabricating it.

Examples of such efforts are disclosed in U.S. Pat. Nos. 5,302,127; 5,169,308; 5,108,288; 5,106,300; and 5,100,323. These are characterized by limitations and disadvantages of ineffectiveness in preventing rotation; complex and costly assemblies of excessive numbers of special components; and complications of disassembly when required for replacement or repair of a dental prosthesis.

SUMMARY OF THE INVENTION

The dental implant of this invention utilizes an abutment provided with an axial bore for receiving a coping screw which secures the abutment to an implant fixture, the axial bore including at least one longitudinal groove arranged to slidably receive a tab extending laterally from the enlarged head of a locking key having a non-circular shank receivable slidably in a correspondingly non-circular bore in the coping screw, whereby the locking key secures the coping screw positively to both the implant fixture and the abutment.

It is the principal objective of this invention to provide a dental implant abutment screw lock of the class described that overcomes the aforementioned limitations and disadvantages of prior dental implant abutment screw locks.

Another objective of this invention is the provision of a dental implant abutment screw lock of the class described that employs a minimum of components of simplified design for economical manufacture and ease of installation.

Still another objective of this invention is to provide a dental implant abutment screw lock of the class described in which the locking key is readily removable to allow removal of the coping screw and detachment of the abutment from the implant fixture.

The foregoing and other objects and advantages of this invention will appear from the following detailed description taken in connection with the accompanying drawings of a preferred embodiment.

BRIEF DESCRIPTION OF THE DRAWINGS

FIG. 1 is an exploded perspective view illustrating the cooperative disposition of components of a dental implant embodying the features of this invention.

FIG. 2 is a longitudinal section of the assembled components forming the dental implant of FIG. 1 and mounting a dental crown shown in broken lines.

DESCRIPTION OF THE PREFERRED EMBODIMENT

The drawings illustrate a dental implant 10, preferably of titanium, which is configured for installation in an opening formed in a jawbone B. The outer, superior end of the implant is formed with a projecting connector 12 of hexagonal or other non-circular configuration. Extending through the connector and a portion of the implant is an axial bore 14 provided with threads 16 by which to releasably secure an abutment 18.

The abutment is provided with an axial bore 20 the inferior end of which is reduced in diameter to provide a shoulder 22. The reduced diameter bore 24 is contoured to the non-circular shape of the connector 12, whereby the implant and abutment are secured together against relative axial rotation.

A coping screw 26 is provided with an elongated threaded shank 28 and an enlarged head 30. Extending axially through the coping screw head and a portion of the length of the shank is an elongated drive socket bore 32 of hexagonal or other non-circular cross section.

A coping screw locking member 34 is provided with a shank 36 of non-circular cross section matching the shape of the drive socket bore 32 for slidable reception therein. The locking member also includes an enlarged head 38 on the shank, and an elongated locking tab 40 extends from the head in the opposite direction from, but in longitudinal alignment with the shank. The tab projects laterally outward from diametrically opposite sides of the head 38 for sliding reception in locking grooves 42 in the abutment 18.

In the embodiment illustrated, the abutment 18 is provided with at least one pair of locking grooves 42 which are disposed diametrically opposite each other and extend longitudinally from the superior end of the abutment to the shoulder 22. A second pair of locking grooves 42' is provided in the abutment, positioned perpendicular to the first pair 42. Thus, the locking tab 40 on the head of the locking member may be received slidably in either pair of locking grooves, as discussed hereinafter.

The locking tab 40 also serves as an extraction tab for removing the locking member from the abutment. The tab preferably is provided with a plurality of longitudinally spaced openings 44, for engagement by a tool in extracting the locking member from the abutment, as described hereinafter.

With the implant 10 secured permanently in a chosen position in the jawbone B, with the raised connector 12 exposed, the abutment 18 is placed on the implant with the raised connector 12 engaged in the non-circular connector 24. The abutment thus is secured against axial rotation relative to the implant.

The coping screw 26 then is inserted through the axial bore 20 and the threaded shank 26 engaged with the threads 16 of bore 14. A drive wrench (not shown) is extended through the bore 20 and engaged with the hex drive socket 32. The wrench is turned to screw the shank 28 into the bore 14 until the head 30 is tightened against the abutment shoulder 22.

Traditionally, coping screws are torqued into position to a manufacturer's specification. This varies from 20 Newton centimeters to 35 Newton centimeters of torque. The phenomenon known as thread relaxation occurs when a screw is torqued into position with the use of forces in the range of 20–35 Newton centimeters. This causes some distortion of the screw threads and this distortion will tend to go back to its original position, thus causing some loosening of the screw. For this purpose, the screw must be re-torqued once thread relaxation has occurred. Once the processing of torquing, thread relaxation and re-torquing has taken place, the screw-implant-fixture interface is rendered stable. However, micro movement of the abutment and implant secondary to dental occlusal forces can set up vibrations within the structure which can allow the thread to unscrew.

The locking member 34 is installed after re-torquing has taken place, to prevent this final ability of the screw to untighten. The final torquing is done so that the locking grooves and the locking tab 40 are aligned. Thus, the locking tab is placed into one of the pair of grooves 42 or 42' and then the shank 36 is inserted into the correspondingly non-circular drive socket 32 of the coping screw 26. The locking member thus secures the coping screw against loosening.

In the embodiment illustrated, the coping screw drive socket 32 is of hexagonal shape and the locking groove pairs 42 and 42' are disposed perpendicular to each other. Accordingly, the coping screw 26 need only be turned 30° in order to align the locking tab 40 with one or the other of the pair of locking grooves 42 or 42'.

It will be apparent that additional diametrically disposed pairs of locking grooves may be provided in the abutment, in order to reduce the turning of the coping screw to less than 30° in order to match the locking tab 40 with a pair of locking grooves.

After the abutment has been installed on the implant fixture 10 the hollow bore 20 may be filled with a temporary material that is capable of being removed easily, preferably without the necessity of drilling. Such filling may be desirable to exclude air, or to secure the locking member 34 against movement within the bore of the abutment. However, filling the bore is not necessary if the locking member extraction tab 40 is cut off flush with the top of the abutment so that the crown C or other restoration will hold the key in place.

In the event it is necessary or desirable to disconnect the abutment 18 from the implant 10, the restoration C is removed and the bore 20 of the abutment is cleaned of any filling material, to expose the extraction tab 40. A tool capable of engaging one of the holes 46 in the tab is inserted through the space between the tab and inner surface of the bore 20 and engaged with an available hole 46. The tool then may be rotated to effect rotation of the locking member 34 and, through the engagement of the locking member shank 36 with the drive socket 32, simultaneous rotation of the coping screw 26. In the alternative, the locking member may be retracted from the abutment bore 20 and a coping screw wrench then is engaged in the drive socket 32 and rotated to remove the screw. In either case, the abutment then may be removed from the implant 10.

The plurality of holes 44 in the extraction tab 40 allows the height of the abutment and tab to be reduced to accommodate installation of a particular prosthesis. Thus, no matter how short the tab becomes, there still exists a hole 44 to be engaged by a retrieval tool. The space between the tab and the wall of the bore 20 allows a retraction tool to be engaged with a hole 44 and then rotated to turn the locking member 34 and coping screw 26 clockwise. This is opposite the direction of rotation to loosen the coping screw. Thus, if forces placed on the entire structure have caused a slight counterclockwise rotation of the coping screw and locking member, wedging of the tab in the slot of the abutment may have occurred, creating a frictional effect to prevent removal of the locking member. By turning the locking member clockwise with the tool, the operator will be able to overcome the wedging and remove the locking member.

From the foregoing, it will be apparent that the dental implant of this invention is of simplified construction, requiring only the provision of the special locking member 34 with locking tab 40, and the locking grooves 42 in the abutment. The implant fixture 10, abutment 18 and coping screw 26 are otherwise of conventional construction.

It will be apparent to those skilled in the art that various changes may be made in the size, shape, type, number and arrangement of parts described hereinbefore. For example, the connector 12 and bore 24 may be reversed. The non-circular configurations of the interengaging shafts and sockets may be of any desired shape other than the hexagonal shape disclosed. More than the two pairs of locking grooves 42, 42' may be provided to reduce the degree of rotation needed to align the locking tab 40 and grooves. Although it is preferred that the tab 40 be sufficiently wide to engage the pair of locking grooves 42, it may be made narrower and a pair of locking pins may project from the head 38 at diametrically opposite positions, to slidably enter the locking grooves. In either case, the tab 40 or pins serve as locking keys to engage the locking grooves. These and other changes may be made, as desired, without departing from the spirit of this invention and the scope of the appended claims.

I claim:

1. A dental implant, comprising:
   a) an implant member configured for anchoring in a jaw bone and having an axial threaded bore therein,
   b) an abutment member having an axial bore therethrough, the bore being of reduced diameter at one end to form a shoulder, and at least one longitudinal locking groove in the wall of the axial bore extending to said shoulder,
   c) interengaging connector means on the implant member and abutment member for securing said members together against relative axial rotation,
   d) a coping screw having a threaded shank removably engaging the threaded bore in the implant member and an enlarged head removably engaging the abutment shoulder and securing the abutment member to the implant member, the coping screw also having a non-circular axial bore therein, and
   e) a locking member having a shank matching the non-circular shape of the axial bore in the coping screw for removable reception therein, the locking member having an enlarged head on the shank received freely in the axial bore of the abutment member, and at least one laterally extending locking key on said locking member head configured to slidably engage the at least one longitudinal locking groove in the abutment member, for securing the abutment member and coping screw against relative axial rotation.

2. The dental implant of claim 1 wherein the abutment member has a pair of substantially diametrically disposed longitudinal locking grooves and the locking member head has a pair of substantially diametrically disposed locking keys slidably engaging the pair of locking grooves.

3. The dental implant of claim 1 wherein the abutment member has a plurality of longitudinal locking grooves forming a plurality of pairs of diametrically disposed locking grooves spaced apart around the circumference of the axial bore, and the locking member head has a pair of diametrically disposed locking keys slidably engaging any one of said pairs of locking grooves.

4. The dental implant of claim 1 wherein the locking member has four longitudinal locking grooves disposed at 90° intervals around the circumference of the axial bore and forming two pairs of diametrically disposed locking grooves, and the locking member head has a pair of substantially diametrically disposed locking keys slidably engaging one or the other of said pairs of locking grooves.

5. The dental implant of claim 4 wherein the non-circular axial bore in the coping screw is hexagonal.

6. The dental implant of claim 1 including an extractor tab projecting from the head of the locking member in the direction opposite the shank thereof, for engagement by an extractor tool to extract the locking member from the axial bore of the abutment member.

7. The dental implant of claim 6 wherein the extractor tab has a plurality of longitudinally spaced openings configured for engagement by an extractor tool.

8. The dental implant of claim 1 wherein a) the abutment member has four longitudinal locking grooves disposed at 90° intervals around the circumference of the axial bore and forming two pairs of diametrically disposed locking grooves, and the locking member head has a pair of substantially diametrically disposed locking keys slidably engaging one or the other of said pairs of locking grooves, b) the non-circular axial bore in the coping screw is hexagonal, c) an extractor tab projects from the head of the locking member in the direction opposite the shank thereof, for engagement by an extractor tool to extract the locking member from the axial bore of the abutment member, and d) the extractor tab has a plurality of longitudinally spaced openings configured for engagement by an extractor tool.

* * * * *